US00PP25089P2

(12) United States Plant Patent
Misato

(10) Patent No.: US PP25,089 P2
(45) Date of Patent: Nov. 18, 2014

(54) ***SENECIO* PLANT NAMED 'SUNSENESUBU'**

(50) Latin Name: *Senecio cruentus*
Varietal Denomination: Sunsenesubu

(71) Applicant: Tomoya Misato, Shiga (JP)

(72) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 113 days.

(21) Appl. No.: 13/694,500

(22) Filed: Dec. 6, 2012

(51) Int. Cl.
*A01H 5/00* (2006.01)

(52) U.S. Cl.
USPC ..... Plt./480

(58) Field of Classification Search
USPC ..... Plt./480
See application file for complete search history.

*Primary Examiner* — Susan McCormick Ewoldt
(74) *Attorney, Agent, or Firm* — C. A. Whealy

(57) ABSTRACT

A new and distinct cultivar of *Senecio* plant named 'Sunsenesubu', characterized by its upright and uniformly mounded plant habit; freely branching growth habit; freely flowering habit; and large daisy-type inflorescences with vivid violet blue-colored ray florets and darker-colored disc florets.

1 Drawing Sheet

Botanical designation: *Senecio cruentus.*
Cultivar denomination: 'SUNSENESUBU'.

BACKGROUND OF THE INVENTION

The present invention relates to a new and distinct cultivar of *Senecio* plant, botanically known as *Senecio cruentus*, and hereinafter referred to by the name 'Sunsenesubu'.

The new *Senecio* plant is a product of a planned breeding program conducted by the Inventor in Higashiomi, Shiga, Japan. The objective of the breeding program is to create new upright and uniformly mounding *Senecio* plants with numerous attractive inflorescences.

The new *Senecio* plant originated from a cross pollination conducted by the Inventor in March, 2008 of a proprietary selection of *Senecio cruentus* identified as code name KP5, not patented, as the female, or seed, parent with a proprietary selection of *Senecio cruentus* identified as code name SNB, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February, 2009.

Asexual reproduction of the new *Senecio* plant by terminal cuttings in a controlled greenhouse environment in Higashiomi, Shiga, Japan since February, 2009 has shown that the unique features of this new *Senecio* plant are stable and reproduced true to type in successive generations.

SUMMARY OF THE INVENTION

Plants of the new *Senecio* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunsenesubu'. These characteristics in combination distinguish 'Sunsenesubu' as a new and distinct *Senecio* plant:

1. Upright and uniformly mounded plant habit.
2. Freely branching growth habit.
3. Freely flowering habit.
4. Large daisy-type inflorescences with vivid violet blue-colored ray florets and darker-colored disc florets.

Plants of the new *Senecio* can be compared to plants of the female parent selection. Plants of the new *Senecio* differ from plants of the female parent selection in the following characteristics:

1. Plants of the new *Senecio* have smaller inflorescences than plants of the female parent selection.
2. Plants of the new *Senecio* and the female parent selection differ in ray floret color as plants of the female parent selection have pink-colored ray florets.

Plants of the new *Senecio* can be compared to plants of the male parent selection. Plants of the new *Senecio* differ from plants of the male parent selection in the following characteristics:

1. Plants of the new *Senecio* have smaller inflorescences than plants of the male parent selection.
2. Plants of the new *Senecio* and the male parent selection differ in ray floret color as plants of the male parent selection have bluish purple-colored ray florets.

Plants of the new *Senecio* can be compared to plants of *Senecio cruentus*×*Senecio heritieri* 'Sunsenevio', disclosed in U.S. Plant Pat. No. 22,274. In side-by-side comparisons conducted in Higashiomi, Shiga, Japan, plants of the new *Senecio* differed from plants of 'Sunsenevio' in the following characteristics:

1. Plants of the new *Senecio* were shorter than and not as upright as plants of 'Sunsenevio'.
2. Plants of the new *Senecio* had smaller and darker green-colored leaves than plants of 'Sunsenevio'.
3. Plants of the new *Senecio* flowered two weeks earlier than plants of 'Sunsenevio'.
4. Plants of the new *Senecio* were more freely flowering than plants of 'Sunsenevio'.
5. Plants of the new *Senecio* and 'Sunsenevio' differed in ray floret color as plants of 'Sunsenevio' had purple violet-colored ray florets.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph at the top of the sheet comprises a side perspective view of a typical flowering plant of 'Sunsenesubu' grown in a container.

The photograph at the bottom of the sheet is a close-up view of a typical flowering plant of 'Sunsenesubu'.

DETAILED BOTANICAL DESCRIPTION

The aforementioned photographs, following observations and measurements describe plants grown during the winter in 15-cm containers in an outdoor nursery in Higashiomi, Shiga, Japan and under cultural practices which approximate those generally used in commercial *Senecio* production. During the production of the plants, day temperatures averaged 10° C. and night temperatures averaged 5° C. Measurements and numerical values represent averages for typical flowering plants. Plants were six months old when the photographs and description were taken. In the following description, color references are made to The Royal Horticultural Society Colour Chart, 2007 Edition, except where general terms of ordinary dictionary significance are used.

Botanical classification: *Senecio cruentus* 'Sunsenesubu'.

Parentage:

*Female, or seed, parent*.—Proprietary selection of *Senecio cruentus* identified as code name KP5, not patented.

*Male, or pollen, parent*.—Proprietary selection of *Senecio cruentus* identified as code name SNB, not patented.

Propagation:

*Type*.—Terminal vegetative cuttings.

*Time to initiate roots, summer and winter*.—About one week at 18° C. to 20° C.

*Time to produce a rooted young plant, summer and winter*.—About four weeks at 18° C. to 20° C.

*Root description*.—Fine, fibrous; white in color.

*Rooting habit*.—Freely branching.

Plant description:

*Plant form and growth habit*.—Upright and uniformly mounded plant habit; daisy-type inflorescences positioned above the foliar plane; freely branching habit; vigorous growth habit.

*Plant height*.—About 25.7 cm.

*Plant diameter*.—About 38 cm.

*Lateral branches*.—Length: About 26.4 cm. Diameter: About 3.1 mm. Internode length: About 1.9 cm. Strength: Strong. Texture: Sparsely pubescent. Color: Close to 138A tinted with close to 79B.

*Foliage description*.—Arrangement: Alternate, simple. Length: About 5.5 cm. Width: About 6 cm. Shape: Cordate. Apex: Obtuse. Base: Cordate. Margin: Palmately lobed; shallowly dentate; slightly undulate. Texture, upper surface: Sparsely pubescent. Texture, lower surface: Densely pubescent. Venation pattern: Pinnate; reticulate. Color: Developing leaves, upper surface: Close to 137B. Developing leaves, lower surface: Close to 147C. Fully expanded leaves, upper surface: Close to N137A; venation, close to 145A. Fully expanded leaves, lower surface: Close to 148B; venation, close to 145B. Petioles: Length: About 4.7 cm. Diameter: About 2.3 mm. Texture, upper and lower surfaces: Sparsely pubescent. Color, upper and lower surfaces: Close to 138A tinted with close to 79B.

Inflorescence description:

*Appearance*.—Large daisy-type inflorescences with narrowly elliptic-shaped ray florets; inflorescences arising from upper leaf axils and positioned above the foliar plane; disc and ray florets developing acropetally on a capitulum; inflorescences face upright and outwardly; freely flowering habit with about 113 inflorescences developing per plant.

*Fragrance*.—None detected.

*Natural flowering season*.—Plants of the new *Senecio* begin flowering about 26 weeks after planting; plants flower continuously from winter to late spring in Japan.

*Inflorescence longevity*.—Inflorescences last about two weeks on the plant; inflorescences persistent.

*Inflorescence buds*.—Height: About 5.8 mm. Diameter: About 6 mm. Shape: Globose. Color: Close to N89C.

*Inflorescence size*.—Diameter: About 5.9 cm. Depth (height): About 8.9 mm. Disc diameter: About 1.3 cm.

*Ray florets*.—Shape: Narrowly elliptic. Length: About 2.2 cm. Width: About 1.1 cm. Apex: Acute or praemorse. Base: Obtuse. Margin: Entire. Texture, upper and lower surfaces: Smooth, glabrous; satiny. Number of ray florets per inflorescence: About 13 in a single whorl. Color: When opening and fully opened, upper surface: Close to N89C; color does not fade with development. When opening and fully opened, lower surface: Close to 97C; longitudinal stripes, close to N89C.

*Disc florets*.—Shape: Tubular; apex dentate, five-pointed. Length: About 7.7 mm. Diameter: About 1.4 mm. Number of disc floret per inflorescence: About 125. Color, immature and mature: Close to 93A.

*Phyllaries*.—Quantity per inflorescence: About 14 in a single whorl. Length: About 7.3 mm. Width: About 1.8 mm. Shape: Lanceolate. Apex: Acute. Base: Fused. Margin: Entire. Texture, upper and lower surfaces: Smooth, glabrous. Color, upper surface: Close to 138A. Color, lower surface: Close to 144B.

*Peduncles*.—Length: About 3.3 cm. Diameter: About 1.7 mm. Strength: Strong. Aspect: Upright to somewhat outwardly. Texture: Smooth, glabrous. Color: Close to 144A and N138B; at the apex, tinted with close to N79A.

*Reproductive organs*.—Androecium: Present on disc florets only. Anther shape: Ellipsoidal. Anther color: Close to 93A. Pollen amount: Abundant. Pollen color: Close to 14A. Gynoecium: Present on both ray and disc florets. Stigma shape: Bi-parted. Stigma color: Close to 93A.

*Seeds and fruits*.—Seed and fruit development have not been observed on plants of the new *Senecio*.

Disease & pest resistance: Plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sunsenesubu' as illustrated and described.

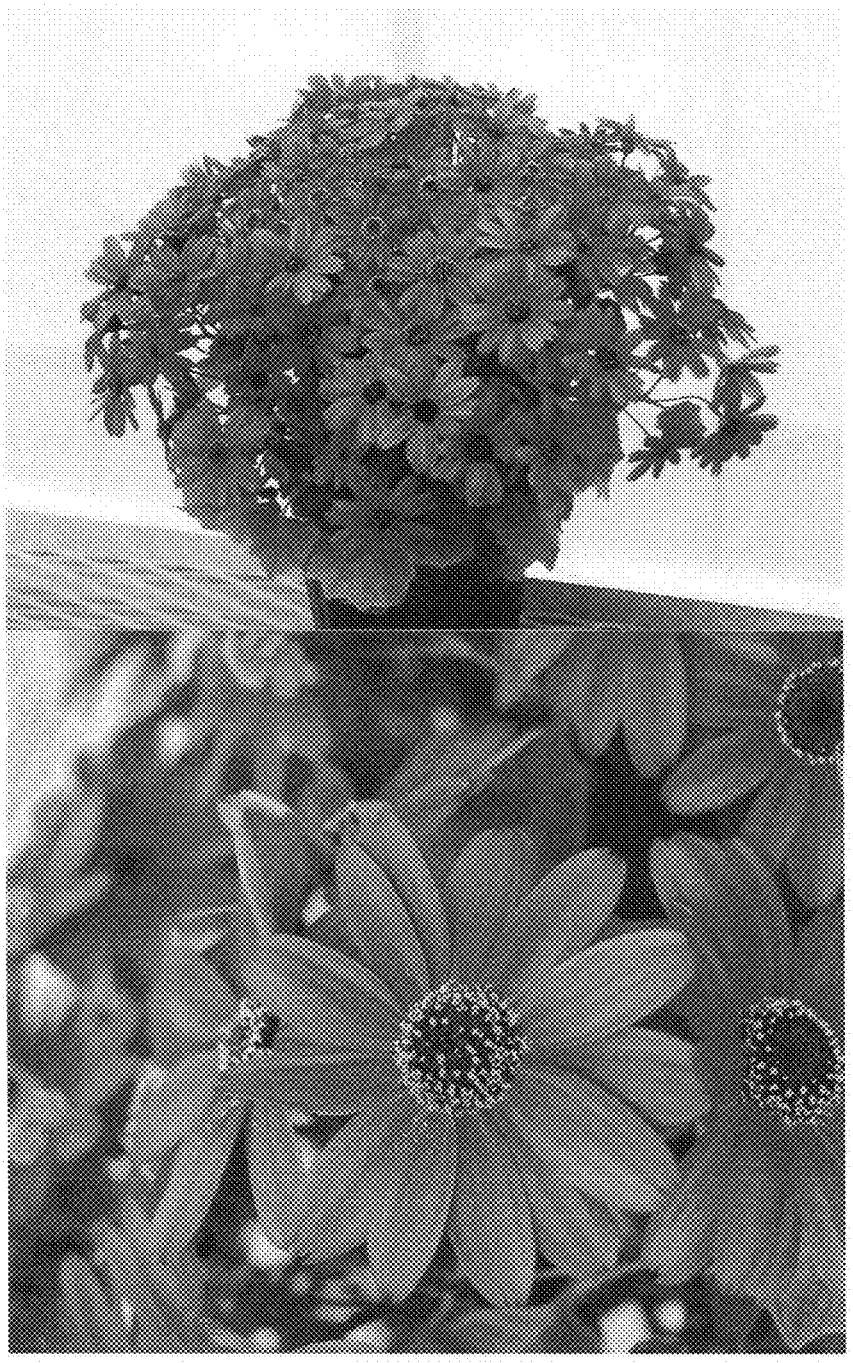

* * * * *